United States Patent [19]

Eliason et al.

[11] Patent Number: 5,302,727
[45] Date of Patent: Apr. 12, 1994

[54] MULTIDRUG RESISTANCE MODIFYING DITHIANES

[75] Inventors: James F. Eliason, Yokohama, Japan; Henri Ramuz, Birsfelden, Switzerland; Franz A. Kaufmann-Schmid, deceased, late of Möhlin, Switzerland, by Beatrice Elvira Kaufmann-Schmid; Stephan F. Kaufmann-Schmid; Andrea R. Kaufmann-Schmid, all of heir

[73] Assignee: Hoffmann-La Roche Inc., Nutley, N.J.

[21] Appl. No.: 914,241

[22] Filed: Jul. 15, 1992

[30] Foreign Application Priority Data

Jul. 18, 1991 [CH] Switzerland ............... 2144/91

[51] Int. Cl.$^5$ .................................. C07D 339/08
[52] U.S. Cl. ......................................... 549/22
[58] Field of Search .................. 549/22; 514/436

[56] References Cited

U.S. PATENT DOCUMENTS

| 4,003,914 | 1/1977 | Ramuz | 549/22 |
| 4,073,797 | 2/1978 | Ramuz | 549/22 |
| 4,127,588 | 11/1978 | Ramuz | 549/22 |

OTHER PUBLICATIONS

Tsuruo et al., Cancer Res. 41:1967–1972 (1981).
Ramuz et al., Eur. J. Med. Chem. 24:493–496 (1989).

*Primary Examiner*—Richard L. Raymond
*Attorney, Agent, or Firm*—George M. Gould; William H. Epstein; Catherine R. Roseman

[57] ABSTRACT

Compounds of the formula

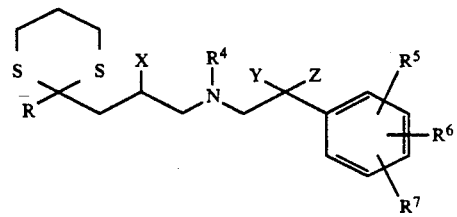

wherein R is a residue of the formula

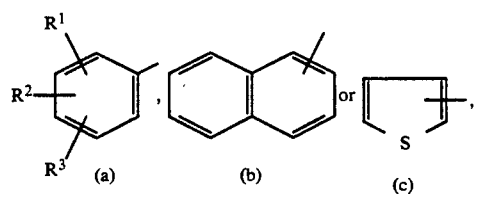

and $R^1$, $R^2$, $R^3$, $R^4$, $R^5$, $R^6$, $R^7$, X, Y and Z are as described, with the exception of rac-N-(3,4-dimethoxyphenethyl)-2-(3,4-dimethoxyphenyl)-$\beta$,N-dimethyl-m-dithiane-2-propanamine, as well as their acid addition salts, in particular for use in eliminating cytostatic resistance in tumor treatment and chloroquine resistance in malaria.

11 Claims, No Drawings

MULTIDRUG RESISTANCE MODIFYING DITHIANES

BACKGROUND OF THE INVENTION

The main reason for failure in the treatment of cancer patients is resistance to conventional chemotherapeutics. One type of drug resistance is referred to as multiple resistance to cytostatics (multidrug resistance); this multiple resistance is characterized by a cross-resistance to functionally and structurally unrelated drugs such as e.g. doxorubicin, vincristine, vinblastine, colchicine and actinomycin D. The gene which is responsible for multiple resistance codes for a glycoprotein, named Pgp, which operates as an energy-dependent outflow pump for cytostatics. Some drugs from different therapeutic and chemical classes have a certain activity in partially or completely eliminating multiple resistance. This is described for the calcium channel blocker verapamil [Cancer Res. 41 1967–1972, (1981)], trifluoperazine, a calmodulin antagonist [Cancer Res. 42, 4730–4733, (1982)], quinidine, an antiarrhythmic [Cancer Res. 44, 4303–4307, (1984)], the immunosuppressor cyclosporin A [Br. J. Cancer 54, 235–238, (1986)] and rac-N-(3,4-dimethoxyphenethyl)-N-methyl-2-(2-naphthyl)-m-dithiane-2-propanamine, a calcium channel blocker [Eur. J. Med. Chem. 24, 493–496, (1989)].

Verapamil, trifluoperazine, quinidine and cyclosporin A, which are used as specific drugs in everyday therapy, are not suitable as drugs for the control of multiple resistance because of their main pharmacological activity. rac-N-(3,4-Dimethoxyphenethyl)-N-methyl-2-(2-naphthyl)-m-dithiane-2-propanamine, a relatively toxic naphthalene derivative, has a clearly lower activity vis-à-vis the novel compounds of formula I described herein and has therefore not been used in clinical trials. It has now been found that the compounds of formula I as well as rac-N-(3,4-dimethoxyphenethyl)-2-(3,4-dimethoxyphenyl)-$\beta$,N-dimethyl-m-dithiane-2-propanamine [U.S. Pat. No. 4,003,914], which is known as a coronary dilator, have outstanding properties as multiple resistance-modifying drugs and can accordingly be used successfully in the therapy of malignant tumors in combination with the usual cytostatics.

SUMMARY OF THE INVENTION

The present invention is concerned with sulphur-containing compounds. In particular, it is concerned with compounds (dithianes) of the general formula

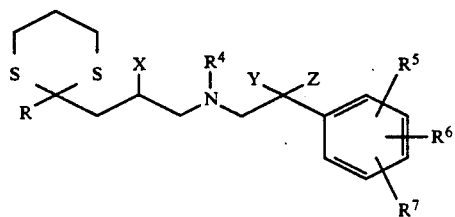

I wherein R is a residue of the formula

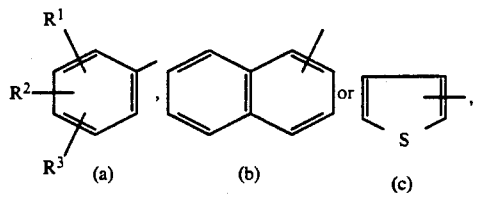

$R^1$, $R^2$ and $R^3$ are individually hydrogen, halogen, lower alkyl, lower alkoxy, aryl-lower-alkoxy, lower alkylthio, trifluoromethyl or di-lower-alkylamino or when two of these residues are adjacent substituents, these substituents can additionally be taken together to form methylenedioxy, ethylenedioxy, trimethylene or tetramethylene; $R^4$ is lower alkyl; $R^5$, $R^6$ and $R^7$ are individually hydrogen, halogen, lower alkyl, lower alkoxy or aryl-lower-alkoxy or when two of these residues are adjacent substituents, these substituents can additionally be taken together to form methylenedioxy or ethylenedioxy; X is hydrogen or lower alkyl; and Y and Z are individually hydrogen or lower alkyl or when taken together form di-, tri-, tetra- or pentamethylene; with the proviso that X and Z are not both hydrogen and rac-N-(3,4-dimethoxyphenethyl)-2-(3,4-dimethoxyphenyl)-$\beta$,N-dimethyl-m-dithiane-2-propanamine is excluded; and acid addition salts thereof.

These compounds are novel and are distinguished by valuable pharmacodynamic properties. For example, they are useful for tumor treatment in combination with cytostatic drugs due to their ability to reduce multiple drug resistance.

DETAILED DESCRIPTION OF THE INVENTION

Objects of the present invention are the compounds of formula I, their pharmaceutically usable acid addition salts, and their use as therapeutically active substances. Manufacture of these compounds, medicaments containing these compounds and the manufacture of such medicaments are also included. Also objects of this invention are use of compounds of formula I and their pharmaceutically usable acid addition salts in the control or prevention of illnesses or in the improvement of health, especially for reducing and/or eliminating multiple resistance to cytostatics in the treatment of tumors or for reducing and/or eliminating chloroquine resistance in the treatment of malaria. The use of rac-N-(3,4-dimethoxyphenethyl)-2-(3,4-dimethoxyphenyl)-$\beta$,N-dimethyl-m-dithiane-2-propanamine and its pharmaceutically usable acid addition salts for reducing and/or eliminating multiple resistance to cytostatics in the treatment of tumors or for reducing and/or eliminating chloroquine resistance in the treatment of malaria and, respectively, for the manufacture of corresponding medicaments are also objects of the present invention.

The term "lower alkyl" used in the present description is straight-chain and branched saturated hydrocarbon residues with 1–4 carbon atoms, i.e. methyl, ethyl, n-propyl, isopropyl, n-butyl, isobutyl, sec.-butyl and tert.-butyl. The term "lower alkoxy" is lower alkyl ether groups in which the term "lower alkyl" has the above significance, i.e. methoxy, ethoxy, n-propoxy, isopropoxy, n-butoxy, isobutoxy, sec.-butoxy and tert.-butoxy. The term "halogen" embraces the 4 halogen atoms fluorine, chlorine, bromine and iodine. The term "aryl" is unsubstituted and substituted phenyl, whereby halogen, lower alkyl and lower alkoxy are to be understood as substituents. The term "leaving group" is known groups such as halogen, preferably chlorine or bromine, and the like.

Those compounds of formula I in which $R^4$ is methyl are preferred. X is preferably methyl and the carbon atom to which this methyl is attached has the (R,S)-, (R)- or (S)-configuration, particularly the (R)- or (S)-configuration. Further, there are preferred those compounds of formula I in which R is a residue of formula (a) or (b), particularly a residue of formula (a) in which one of the residues $R^1$, $R^2$ and $R^3$ is hydrogen and the other two residues each are lower alkoxy, especially methoxy, or when they are adjacent can be taken together to form methylenedioxy or ethylenedioxy, or two of the residues $R^1$, $R^2$ and $R^3$ are hydrogen and the third residue is halogen, especially chlorine. Also preferred are those compounds of formula I in which one of the residues $R^5$, $R^6$ and $R^7$ is hydrogen and the other two residues each are lower alkoxy, especially methoxy, or when they are adjacent can be taken together to form methylenedioxy or ethylenedioxy, or two of the residues $R^5$, $R^6$ and $R^7$ are hydrogen and the third residue is halogen, especially chlorine, lower alkyl, especially methyl, or lower alkoxy, especially methoxy. Preferably, Y and Z both are hydrogen or can be taken together to form di-, tri-, tetra- or pentamethylene.

From the above it will be evident that there are particularly preferred those dithianes of formula I which can be represented by the following formula:

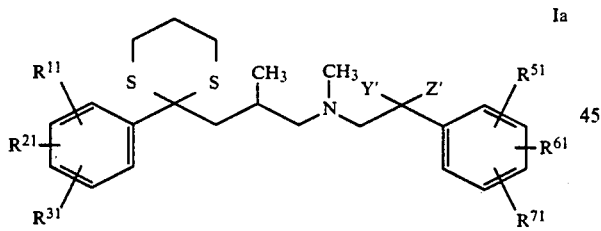

wherein one of the residues $R^{11}$, $R^{21}$ and $R^{31}$ is hydrogen and the other two residues are methoxy or when they are adjacent can be taken together to form methylenedioxy or ethylenedioxy or two of the residues $R^{11}$, $R^{21}$ and $R^{31}$ are hydrogen and the third residue is chlorine, one of the residues $R^{51}$, $R^{61}$ and $R^{71}$ is hydrogen and the other two residues are methoxy or when they are adjacent can be taken together to form methylenedioxy or ethylenedioxy or two of the residues $R^{51}$, $R^{61}$ and $R^{71}$ are hydrogen and the third residue is chlorine, methyl or methoxy and Y' and Z' both are hydrogen or together are di-, tri-, tetra- or pentamethylene, and acid addition salts of such compounds.

Also preferred are those dithianes of formula I which can be represented by the following formula:

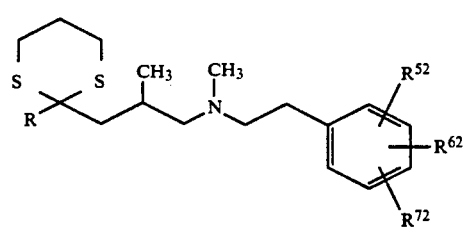

wherein R is a residue of the formula

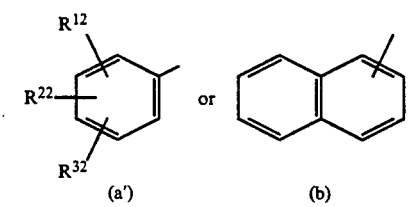

one of the residues $R^{12}$, $R^{22}$ and $R^{32}$ is hydrogen or halogen and the other two residues are methoxy or hydrogen; and one of the residues $R^{52}$, $R^{62}$ and $R^{72}$ is hydrogen or halogen and the other two residues are methoxy or hydrogen, and acid addition salts of such compounds.

Additionally preferred are those dithianes of formula I which can be represented by the following formula:

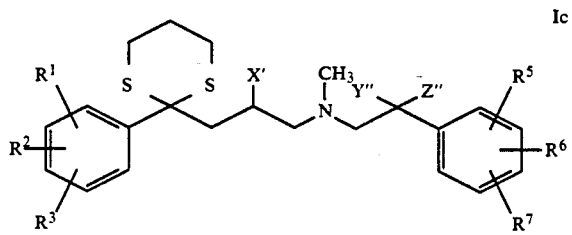

wherein $R^1$, $R^2$, $R^3$, $R^5$, $R^6$ and $R^7$ are as described; X' is hydrogen or methyl and Y" and Z" taken together form di-, tri-, tetra- or pentamethylene, and acid addition salts of such compounds.

Specially preferred compounds of formula I are:
N-[[1-(3,4-Dimethoxyphenyl)cyclohexyl]methyl]-2-(3,4-dimethoxyphenyl)-N-methyl-m-dithiane-2-propanamine,
rac-N-[[1-(3,4-dimethoxyphenyl)cyclohexyl]methyl]-β,N-dimethyl-2-(3,4,5-trimethoxyphenyl)-m-dithiane-2-propanamine,
2-(3,4-dimethoxyphenyl)-N-[[1-(3,4-dimethoxyphenyl)cyclopentyl]methyl]-N-methyl-m-dithiane-2-propanamine,
rac-2-(4-chlorophenyl)-N-[[1-(4-chlorophenyl)cyclobutyl]-methyl]-β,N-dimethyl-m-dithiane-2-propanamine,
(S)-(+)-2-(3,4-dimethoxyphenyl)-N-[[1-(3,4-dimethoxy-phenyl)cyclobutyl]methyl]-β,N-dimethyl-m-dithiane-2-propanamine,
(R)-(−)-2-(3,4-dimethoxyphenyl)-N-[[1-(3,4-dimethoxy-phenyl)cyclobutyl]methyl]-β,N-dimethyl-m-dithiane-2-propanamine,
(R)-(−)-N-(3,4-dimethoxyphenethyl)-2-(3,4-dimethoxyphenyl)-β,N-dimethyl-m-dithiane-2-propanamine,
(S)-(+)-N-(3,4-dimethoxyphenethyl)-2-(3,4-dimethoxyphenyl)-β,N-dimethyl-m-dithiane-2-propanamine, rac-N-(4-chlorophenethyl)-2-(4-chlorophenyl)-β, N-dimethyl-m-dithiane-2-propanamine and rac-N-(3,4-dimethoxyphenethyl)-β, N-dimethyl-2-(2-naphthyl)-m-dithiane-2-propanamine.

Also preferred are the acid addition salts of these compounds, especially hydrochlorides, methanesulphonates, amidosulphonates, ascorbates, and oxalates.

The process in accordance with the invention for the manufacture of compounds of formula I comprises reacting a compound of the general formula

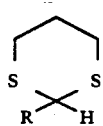

II wherein R has the significance given above, with a compound of the general formula

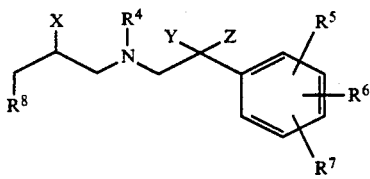

III wherein $R^8$ is a leaving group and X, Y, Z, $R^4$, $R^5$, $R^6$ and $R^7$ have the significance given above, and if desired, resolving a racemic compound of formula I obtained into the corresponding enantiomers and/or, if desired, converting a compound of formula I obtained into a pharmaceutically usable acid addition salt.

The reaction of a compound of formula II with a compound of formula III can be carried out in a manner known per se. Conveniently, the reaction is effected in an organic solvent which is inert under the reaction conditions and at a temperature between about −80° C. and a temperature of 40° C., preferably between about −20° C. and room temperature. Ethers such as abs. tetrahydrofuran and abs. diethyl ether and the like come into consideration as solvents. The reaction is effected in the presence of a strong base such as butyllithium and the like.

The compounds of formula II above which are used as starting materials are known. The compounds of formula III above are partly known and partly still novel. Thus, those compounds in which Y and Z are different from hydrogen and/or X is lower alkyl are novel. These can be prepared in a manner known per se, i.e. in an analogous manner to the preparation of the known compounds.

The compounds of formula I can be converted into acid addition salts, for example by treatment with an inorganic acid such as a hydrohalic acid, for example hydrochloric or hydrobromic acid, sulphuric acid, phosphoric acid and the like or with an organic acid such as oxalic acid, malonic acid, succinic acid, amidosulphonic acid, fumaric acid, maleic acid, ascorbic acid, salicylic acid, tartaric acid, citric acid, methanesulphonic acid, benzenesulphonic acid, camphorsulphonic acid, ethanedisulphonic acid, anthraquinone-1,5-disulphonic acid (Journal of Pharmaceutical Sciences, 1977, Vol. 66, pages 1-16) and the like. Examples of acid addition salts include hydrochlorides, methanesulphonates, amidosulphonates, ascorbates, and oxalates.

The compounds of formula I may be used in a method for treating tumors with two or more unrelated drugs, which reduces cross-resistance induced by one drug to the other, by administering a compound of formula I in an amount effective to reduce or eliminate such cross resistance. Drugs such as cytostatics are particularly contemplated, for example, doxorubicin, vincristine, vinblastine, colchicine, and actinomycin D.

A method for treating malaria, in particular with chloroquine, in which resistance to chloroquine is reduced, also uses an amount of a compound of formula I effective to reduce the resistance.

Of the acid addition salts of the compounds of formula I there are preferred those which are pharmaceutically usable. If an acid addition salt of a compound of formula I is obtained in the course of the process in accordance with the invention, then such a salt can be converted in a known manner, e.g. by treatment with alkali, into the corresponding free base and, if desired, this can be converted into another acid addition salt.

Those compounds of formula I which contain an asymmetric carbon atom can be present in racemic form or in optically active form and not only the racemic forms but also the optically active forms are objects of the present invention.

These optically active compounds can be obtained by reacting the racemate with a chiral acid, separating the thus-obtained mixture of diastereomeric salts, liberating from the thus-obtained salts the two bases and, if desired, converting these with an acid into their pharmaceutically usable acid addition salts. Since the compounds of formula I and their acid addition salts generally crystallize only with considerable difficulty, this procedure in the scope of the present invention is not preferred. Rather, it is preferred to manufacture these optically active compounds by introducing the desired chiral centre at the very beginning of the synthesis, namely using an alkyl halide of formula IV

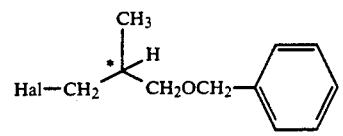

IV which is described in the literature [Helv. Chim. Acta 60, 925-944, (1977)] and which is chirally labelled in the foregoing formula with an asterisk, whereby the subsequent reaction steps for the preparation of compounds of the general formula

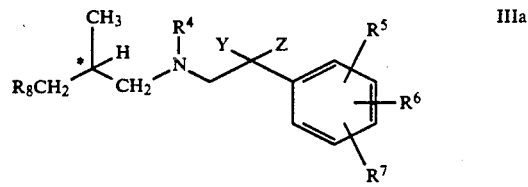

IIIa wherein Y, Z, $R^5$, $R^6$, $R^7$ and $R^8$ have the significance given above, can be carried out in a manner known per se.

The modifying activity of multiple resistance to cytostatics of the compounds of formula I, of rac-N-(3,4-dimethoxyphenethyl)-2-(3,4-dimethoxyphenyl)-β,N-dimethyl-m-dithiane-2-propanamine and of usual reference substances was investigated as follows:

KB-8-5 cells, a human cell line with multiple resistance to cytostatics, and KB-3-1 cells, a correspondingly sensitive cell line [Cell. Mol. Genet. 11, 117–126, (1985) and Science 232, 643–645, (1986)], were cultivated in suitable media [Cancer Res. 94, 267–275, (1984), Exp. Hematol. 12, 559–567, (1984), Eliason, Ramuz & Kaufmann in Int. J. Cancer 46, 113–117, (1990)].

The biological test is based on the ability of the test substance to lower the concentration of a standard cytostatic which is required to kill 50% of the cells. The testing and the determination of cytotoxicity are based on the ability of living cells to reduce 3-(4,5-dimethyl-thiazol-2-yl)-2,5-diphenyltetrazolium bromide to the corresponding blue formazan (colorimetric measurement) [J. Immunol. Methods 65, 55–63, (1985)]. The cells were incubated for 2 days in separate containers. The compounds selected for the biological investigation were added to the cell cultures in such a manner that the serial concentrations $10^{-8}M$, $10^{-7}M$, $10^{-6}M$, $10^{-5}M$ and $10^{-4}M$ were achieved. Vincristine in 4 dilution series ($3.10^{-9}M$, $10^{-8}M$, $3.10^{-8}M$ and $10^{-7}M$ for KB-8-5 cells and 30 times less for the KB-3-1 cells) was added thereto. After incubating for 5 days the cell count was measured at 540 nm using the formazan color reaction. The evaluation was carried out by calculating a resistance modification index, RMI, which is the ratio between the $IC_{50}$ value of vincristine in the absence of a test substance and the $IC_{50}$ value of vincristine in the presence of a test substance.

$$RMI = \frac{IC_{50} \text{ (control culture)}}{IC_{50} \text{ (culture with test substance)}}$$

In order to compare all activities of compounds from different classes, a $RMI_{0.1}$ is defined: this is the RMI value of a substance which is obtained with the ten-fold lower concentration than the $IC_{50}$ value. ($RMI_{0.1}$ = RMI at $0.1.IC_{50}$ of the substance). The results obtained for some compounds of formula I as well as for (+) and (−)verapamil are compiled in the following Table in which n is the number of experiments. The preliminary toxicological data ($LD_{50}$, mouse) after oral administration of the test compound are also given.

|   | n | $IC_{50}$ (mM) | Vincristine $RMI_{0.1}$ | Toxicity mg · kg$^{-1}$ p.o., mouse |
|---|---|---|---|---|
| A | 2 | 14 | 216 | 1250–2500 |
| B | 2 | 14 | 159 | 625–1250 |
| C | 2 | 21 | 224 | 1000–2000 |
| D | 2 | 21 | 163 | 1000–2000 |
| E | 2 | 7.7 | 24 | 2500–5000 |
| (+) Verapamil | 4 | 62 | 12 | 250–500 |
| (−) Verapamil | 4 | 72 | 47 | 60–120 |

A = rac-2-(4-Chlorophenyl)-N-(3,4-dimethoxyphenethyl)-β, N-dimethyl-m-dithiane-2-propanamine hydrochloride,
B = rac-N-(3,4-dimethoxyphenethyl)-β,N-dimethyl-2-(4-tolyl)-m-dithiane-2-propanamine hydrochloride,
C = rac-N-[[1-(3,4-dimethoxyphenyl)cyclobutyl]methyl]-β,N-dimethyl-2-(3,4,5-trimethoxyphenyl)-m-dithiane-2-propanamine hydrochloride,
D = rac-2-(3,4-dimethoxyphenyl)-N-[[1-(3,4-dimethoxyphenyl)cyclobutyl]methyl]-β,N-dimethyl-m-dithiane-2-propanamine hydrochloride,
E = rac-N-(4-chlorophenethyl)-2-(3,4-dimethoxyphenyl)-β,N-dimethyl-m-dithiane-2-propanamine hydrochloride.

The dithianes of formula I, the rac-N-(3,4-dimethoxyphenethyl)-2-(3,4-dimethoxyphenyl)-β,N-dimethyl-m-dithiane-2-propanamine and their salts have outstanding properties against multiple resistant cells of malignant tumors. These compounds can be used in combination, together or separately, with one or more conventional anticancer drugs such as vinca alkaloids or epipodophyllotoxins (e.g. vincristine, vinblastine, vindesine, etoposine, teniposide), antibiotics (e.g. adriamycin, daunorubicin, bleomycin, mithramicin), interchelators (e.g. amonafide), anti-metabolites (e.g. fluorouracil) or alkylating agents (e.g. cyclophosphamide, cisplatin). The invention is accordingly also concerned with products containing one of these compounds and a cytostatic as combination preparations for the simultaneous, separate or planned stepwise use in cytostatic therapy. Both the formation of primary tumors, and the formation of metastases are prevented or greatly restricted by the novel combinations. As mentioned, these compounds can be administered together or separately with the cytostatics. However, the separate prior application of these compounds, which is effected by oral administration, is preferred, while the cytostatics are given orally or parenterally. The cytostatics can be dosed in a smaller amount or in a similar amount as in conventional therapy. The dosage of these compounds depends on the age, condition and weight of the patient and on the mode of application. As a rule, the dosage of active ingredient is about 1 to 50 mg.kg$^{-1}$ body weight in the case of oral administration and about 0.1 mg to 3 mg.kg$^{-1}$ body weight in the case of parenteral administration in a bolus injection or in the case of a slow intravenous infusion. The indicated dosages are, however, to be understood only as examples and can be adjusted according to the severity of the indication under treatment as judged by the treating physician.

The compounds of formula I and their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions. As mentioned earlier, medicaments containing a compound of formula I or a pharmaceutically usable acid addition salt thereof are also an object of the present invention, furthermore also a process for the manufacture of such medicaments which is characterized by bringing one or more compounds of formula I and/or a pharmaceutically usable acid addition salt thereof and, if desired, one or more therapeutically inert, inorganic or organic excipients into a galenical administration form.

Lactose, corn starch or derivatives thereof, talc, stearic acid or its salts and the like can be used e.g. as excipients for the manufacture of tablets, coated tablets, dragées and hard gelatine capsules. Suitable excipients for soft gelatine capsules are e.g. vegetable oils, waxes, fats, semi-solid and liquid polyols and the like. Suitable excipients for the manufacture of solutions are e.g. water, polyols, saccharose, invert sugar, glucose and the like. Suitable excipients for injections solutions are e.g. water, alcohols, polyols, glycerol, vegetable oils and the like. Suitable excipients for suppositories are e.g. natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

The following Examples are intended to illustrate the present invention, but are not limiting in any manner. All temperatures are given in degrees Centigrade.

EXAMPLE 1

(A) A solution of 18.6 g (0.0759 mol) of 1-(3,4-dimethoxyphenyl)-1-cyclohexylcarbonitrile [J. Org. Chem. 36, 1308 (1971) in a mixture of 300 ml of abs. methanol and 400 ml of liquid ammonia was treated with 5.0 g of Raney-cobalt and the mixture was hydrogenated in a shaking autoclave at a temperature of 70° and a pressure of $10^7$ Pa. Thereafter, the mixture was cooled to $-20°$ and filtered, and the solution was evaporated under reduced pressure. The residual oil was distilled at 160° and a pressure of 390 Pa, whereby there was obtained 1-(3,4-dimethoxyphenyl)-1-cyclohexanemethanamine as a colourless oil which was used directly in the next step.

(B) A solution of 7.73 g (0.031 mol) of 1-(3,4-dimethoxyphenyl)-1-cyclohexanemethanamine, 4.3 ml (0.00348 mol) of N-ethylmorpholine and 0.3 g of dimethylaminopyridine in 100 ml of abs. tetrahydrofuran was cooled to $-10°$ and treated within 10 minutes with 4.4 ml (0.0348 mol) of isobutyl chloroformate. The mixture was then stirred at room temperature for 18 hours and filtered, and the solution was evaporated under reduced pressure. The residue was dissolved in ethyl acetate and the organic solution was washed first with 1N hydrochloric acid and then with a saturated sodium bicarbonate solution, dried over magnesium sulphate and evaporated under reduced pressure. tetrahydrofuran and 2.35 g (0.062 mol) of lithium aluminium hydride and the mixture was heated to reflux for 2 hours, thereafter cooled and treated with a saturated sodium sulphate solution. After filtering the mixture and evaporating the solvent there was obtained an oil which was distilled at 153°/260 Pa, whereby there was obtained 1-(3,4-dimethoxyphenyl)-N-methyl-1-cyclohexanemethanamine as a colourless oil which was used directly in the next step.

(C) A solution of 3.40 g (0.0129 mol) of 1-(3,4-dimethoxyphenyl)-N-methyl-1-cyclohexanemethanamine in 50 ml of abs. dimethylformamide was treated with 3.57 g (0.0258 mol) of anhydrous potassium carbonate. The mixture was stirred at 5° and treated with 1.4 ml (0.0129 mol) of 1-bromo-3-chloropropane and subsequently stirred initially at 30° for 4 hours and thereafter at room temperature for 16 hours. The solvent was then evaporated at room temperature under reduced pressure and the residue was treated with water. The mixture was extracted three times with ether and the organic extracts were dried over magnesium sulphate, filtered and evaporated under reduced pressure. The oily residue was distilled under a pressure of 300 Pa at 195°, whereby there was obtained N-(3-chloropropyl)-1-(3,4-dimethoxyphenyl)-N-methylcyclohexanemethanamine as a colourless viscous oil which was used directly in the next step.

(D) A solution of 2.56 g (0.01 mol) of 2-(3,4-dimethoxyphenyl)-m-dithiane in 20 ml of abs. tetrahydrofuran was cooled to $-60°$ in a sulphonation flask while gassing with dry argon and treated dropwise within 15 minutes with 4.68 ml (0.0075 mol) of a solution of butyllithium in hexane, whereby the temperature was held at $-60°$. Thereafter, the solution was stirred at $-20°$ for 2 hours, then again cooled to $-60°$ and treated dropwise with a solution of 1.70 g (0.005 mol) of N-(3-chloropropyl)-1-(3,4-dimethoxyphenyl)-N-methylcyclohexanemethanamine in 20 ml of abs. tetrahydrofuran. After 16 hours at $-20°$ and 4 hours at room temperature the solution was poured on to ice-water and the mixture was washed three times with ether. The ethereal extracts were dried over magnesium sulphate, filtered and evaporated under reduced pressure. The residual oil was chromatographed on silica gel 60 with toluene/ethyl acetate (8:2). After evaporation of the solvent there was obtained a colourless oil which was dissolved in a small amount of abs. dioxan and treated with an excess of hydrogen chloride in abs. dioxan, whereby N-[[1-(3,4-dimethoxyphenyl)cyclohexyl]methyl]-2-(3,4-dimethoxyphenyl)-N-methyl-m-dithiane-2-propanamine hydrochloride was obtained as a solid white foam.

$C_{31}H_{45}NO_4S_2\cdot HCl$: Calc: C 62.44, H 7.78, N 2.35%, Found: C 62.68, H 8.16, N 2.28%.

EXAMPLE 2

In an analogous manner to that described in Example 1, paragraph (D), from 2-(3,4,5-trimethoxyphenyl)-m-dithiane and N-(3-chloropropyl)-1-(3,4-dimethoxyphenyl)-N-methylcyclohexanemethanamine there was obtained N-[[1-(3,4-dimethoxyphenyl)cyclohexyl]methyl]-N-methyl-2-(3,4,5-trimethoxyphenyl)-m-dithiane-2-propanamine hydrochloride as a solid.

$C_{32}H_{47}NO_5S_2\cdot HCl$: Calc: C 61.37, H 7.73, N 2.24%, Found: C 61.08, H 8.07, N 2.14%.

EXAMPLE 3

(A) In an analogous manner to that described in Example 1, paragraph (C), from 1-(3,4-dimethoxyphenyl)-N-methyl-1-cyclohexanemethanamine and 1-bromo-2-methyl-3-chloropropane there was obtained rac-N-(3-chloro-2-methylpropyl)-1-(3,4-dimethoxyphenyl)-N-methylcyclohexanemethanamine as a viscous oil which was used directly in the next step.

(B) In an analogous manner to that described in Example 1, paragraph (D), from 2-(3,4-dimethoxyphenyl)-m-dithiane and rac-N-(3-chloro-2-methylpropyl)-1-(3,4-dimethoxyphenyl)-N-methylcyclohexanemethanamine there was obtained rac-N-[[1-(3,4-dimethoxyphenyl)cyclohexyl]methyl]-2-(3,4-dimethoxyphenyl)-β,N-dimethyl-m-dithiane-2-propanamine as a thick oil.

$C_{32}H_{47}NO_4S_2$: Calc: C 66.98, H 8.26, N 2.44%. Found: C 66.89, H 8.29, N 2.43%.

EXAMPLE 4

In an analogous manner to that described in Example 1, paragraph (D), from 2-(3,4,5-trimethoxyphenyl)-m-dithiane and rac-N-(3-chloro-2-methylpropyl)-1-(3,4-dimethoxyphenyl)-N-methylcyclohexanemethanamine there was obtained rac-N-[[1-(3,4-dimethoxyphenyl)cyclohexyl]methyl]-β,N-dimethyl-2-(3,4,5-trimethoxyphenyl)-m-dithiane-2-propanamine as a viscous oil.

$C_{33}H_{49}NO_5S_2$: Calc: C 65.64, H 8.18, N 2.32%. Found: C 65.63, H 8.21, N 2.34%.

EXAMPLE 5

(A) In an analogous manner to that described in Example 1, paragraph (A), from 1-(3,4-dimethoxyphenyl)-1-cyclopentylcarbonitrile [J. Org. Chem. 36, 1308 (1971) ] there was obtained 1-(3,4-dimethoxyphenyl)-1-cyclopentanemethanamine as a colourless oil which was used directly in the next step.

(B) A solution of 13.6 g (0.058 mol) of 1-(3,4-dimethoxyphenyl)-1-cyclopentanemethanamine in 100 ml of abs. methylene chloride was treated within 15 minutes with 8.84 ml (0.0638 mol) of trifluoroacetic anhydride and heated to reflux for 2 hours, whereupon the mixture was cooled and poured on to 300 ml of ice-water. The organic phase was separated, dried over magnesium sulphate and evaporated under reduced pressure. The solid residue was dissolved in a small amount of methylene chloride and the solution was treated portionwise with hexane. There was thus obtained N-[[1-(3,4-dimethoxyphenyl)cyclopentyl]methyl]-2,2,2-trifluoroacetamide as a solid of melting point 109°–110°. MS: 331 (M)+.

(C) A solution of 3.3 g (0.01 mol) of N-[[1-(3,4-dimethoxyphenyl)cyclopentyl]methyl]-2,2,2-trifluoroacetamide in 200 ml of abs. acetone was treated with 1.5 ml (0.0248 mol) of methyl iodide. 2.75 g (0.049 mol) of powdered potassium hydroxide were added portionwise within 30 minutes at a temperature of 10°–12°. After 10 minutes the mixture was filtered and the filtrate was evaporated under reduced pressure. The residue was taken up in a solution of 1.2 g of potassium hydroxide in 100 ml of water. After heating to reflux for one hour the solution was extracted with ether. The organic extracts were dried over magnesium sulphate and evaporated. There was thus obtained 1-(3,4-dimethoxyphenyl)-N-methyl-1-cyclopentanemethanamine as a colourless oil (b.p. 145°/260 Pa) which was used directly in the next step.

(D) In an analogous manner to that described in Example 1, paragraph (C), from 1-(3,4-dimethoxyphenyl)-N-methyl-1-cyclopentanemethanamine and 1-bromo-3-chloropropane there was obtained N-(3-chloropropyl)-1-(3,4-dimethoxyphenyl)-N-methylcyclopentanemethanamine as a viscous oil (b.p. 170°/260 Pa) which was used directly in the next step.

(E) In an analogous manner to that described in Example 1, paragraph (D), from 2-(3,4-dimethoxyphenyl)-m-dithiane and N-(3-chloropropyl)-1-(3,4-dimethoxyphenyl)-N-methylcyclopentanemethanamine there was obtained 2-(3,4-dimethoxyphenyl)-N-[[1-(3,4-dimethoxyphenyl)cyclopentyl]methyl]-N-methyl-m-dithiane-2-propanamine hydrochloride as a solid.

$C_{30}H_{43}NO_4S_2 \cdot HCl$: Calc: C 61.88, H 7.62, N 2.41%; Found: C 61.83, H 8.11, N 2.41%.

EXAMPLE 6

In an analogous manner to that described in Example 1, paragraph (D), from 2-(3,4,5-trimethoxyphenyl)-m-dithiane and N-(3-chloropropyl)-1-(3,4-dimethoxyphenyl)-N-methylcyclopentanemethanamine there was obtained N-[[1-(3,4-dimethoxyphenyl)cyclopentyl]methyl]-N-methyl-2-(3,4,5-trimethoxyphenyl)-m-dithiane-2-propanamine as a viscous oil.

$C_{31}H_{45}NO_5S_2$: Calc.: C 64.66, H 7.88, N 2.43%. Found: C 64.71, H 7.97, N 2.48%.

EXAMPLE 7

(A) In an analogous manner to that described in Example 1, paragraph (C), from 1-(3,4-dimethoxyphenyl)-N-methyl-1-cyclopentanemethanamine and 1-bromo-2-methyl-3-chloropropane there was obtained rac-N-(3-chloro-2-methylpropyl)-1-(3,4-dimethoxyphenyl)-N-methylcyclopentanemethanamine as a viscous oil (b.p. 155°/390 Pa) which was used directly in the next step.

(B) In an analogous manner to that described in Example 1, paragraph (D), from 2-(3,4-dimethoxyphenyl)-m-dithiane and rac-N-(3-chloro-2-methylpropyl)-1-(3,4-dimethoxyphenyl)-N-methylcyclopentanemethanamine there was obtained rac-2-(3,4-dimethoxyphenyl)-N-[[1-(3,4-dimethoxyphenyl)cyclopentyl]methyl]-β,N-dimethyl-m-dithiane-2-propanamine hydrochloride as a solid foam.

$C_{31}H_{46}ClNO_4S_2$: Calc.: C 61.42, H 7.95, N 2.05%. Found: C 61.09, H 7.70, N 1.87%.

EXAMPLE 8

In an analogous manner to that described in Example 1, paragraph (D), from 2-(3,4,5-trimethoxyphenyl)-m-dithiane and rac-N-(3-chloro-2-methylpropyl)-1-(3,4-dimethoxyphenyl)-N-methylcyclopentanemethanamine there was obtained rac-N-[[1-(3,4-dimethoxyphenyl)cyclopentyl]methyl]-β,N-dimethyl-2-(3,4,5-trimethoxyphenyl)-m-dithiane-2-propanamine as a viscous oil.

$C_{32}H_{47}NO_5S_2$: Calc.: C 65.16, H 8.03, N 2.37%, Found: C 64.97, H 8.12, N 2.43%.

EXAMPLE 9

(A) 16.9 g (0.1 mol) of N-methyl-2-(4-chlorophenyl)ethylamine were dissolved in 30 ml of dimethylformamide and treated with 20.7 g (0.3 mol) of anhydrous potassium carbonate. The mixture was stirred at 5° and treated with 12.6 ml (0.11 mol) of 1-bromo-2-methyl-3-chloropropane, whereupon the mixture was stirred at 30° for a further 4 hours, the solvent was evaporated at 30° under reduced pressure and the residue was treated with water. The separated oil was extracted three times with ether. The organic extracts were dried over magnesium sulphate and evaporated under reduced pressure. The residual oil was distilled at 135°–140°/260 Pa, whereby there was obtained rac-4-chloro-N-(3-chloro-2-methylpropyl)-N-methylphenethylamine as a colourless oil which was used directly in the next step. MS: 260 (M)+.

(B) 2.77 g (0.012 mol) of 2-(4-chlorophenyl)-m-dithiane and 10 ml of abs. tetrahydrofuran were cooled to −70° in a sulphonation flask while gassing with argon and treated with 7.50 ml (0.012 mol) of butyllithium in hexane. Thereupon, the mixture was stirred at −20° for 2 hours. A solution of 2.50 g (0.0096 mol) of rac-4-chloro-N-(3-chloro-2-methylpropyl)-N-methylphenethylamine in abs. tetrahydrofuran was added dropwise thereto at −70° within 15 minutes, whereupon the mixture was left to stand at −20° for 18 hours and at room temperature for 3 hours. The reaction solution was then poured into water and extracted three times with ether. The ethereal extracts were dried over magnesium sulphate and evaporated. The residual oil was chromatographed on silica gel with toluene-hexane (1:1). After evaporating the solvent and warming the residue at 50° for 18 hours under reduced pressure there was obtained rac-N-(4-chlorophenethyl)-2-(4-chlorophenyl)-β,N-dimethyl-m-dithiane-2-propanamine as a viscous oil.

$C_{23}H_{29}Cl_2NS_2$: Calc.: C 60.78, H 6.43, N 3.08%, Found: C 60.81, H 6.49, N 3.04%.

EXAMPLE 10

In an analogous manner to that described in Example 9, paragraph (B), from 2-[(3,4-methylenedioxy)phenyl]-m-dithiane and rac-4-chloro-N-(3-chloro-2-methylpropyl)-N-methylphenethylamine there was obtained rac-N-(4-chlorophenethyl)-β-methyl-2-[3,4-(methylenedioxy)phenyl]-m-dithiane-2-propanamine as a viscous oil.

EXAMPLE 11

In an analogous manner to that described in Example 9, paragraph (B), from 2-(3,4-dimethoxyphenyl)-m-dithiane and rac-4-chloro-N-(3-chloro-2-methylpropyl)-N-methylphenethylamine there was obtained rac-N-(4-chlorophenethyl)-2-(3,4-dimethoxyphenyl)-$\beta$,N-dimethyl-m-dithiane-2-propanamine as a viscous oil.

$C_{24}H_{30}ClNO_2S_2$: Calc.: C 62.11, H 6.52, N 3.02% Found: C 62.28, H 6.38, N 2.87%.

$C_{25}H_{34}ClNO_2S_2$: Calc.: C 62.54, H 7.14, N 2.92%, Found: C 62.55, H 7.42, N 2.86%.

EXAMPLE 12

In an analogous manner to that described in Example 9, paragraph (A), from N-methylhomoveratrylamine and rac-1-bromo-2-methyl-3-chloropropane there was obtained rac-N-(3-chloro-2-methylpropyl)-3,4-dimethoxy-N-methylphenethylamine as a colourless oil which was used directly in the next step. MS: 285 (M)+.

In an analogous manner to that described in Example 9, paragraph (B), from 2-(4-chlorophenyl)-m-dithiane and rac-N-(3-chloro-2-methylpropyl)-3,4-dimethoxy-N-methylphenethylamine there was obtained rac-2-(4-chlorophenyl)-N-(3,4-dimethoxyphenethyl)-$\beta$,N-dimethyl-m-dithiane-2-propanamine as a viscous oil.

$C_{25}H_{34}ClNO_2S_2$: Calc.: C 62.54, H 7.14, N 2.94%, Found: C 62.61, H 7.15, H 2.87%.

EXAMPLE 13

In an analogous manner to that described in Example 9, paragraph (B), from 2-(4-tolyl)-m-dithiane and rac-N-(3-chloro-2-methylpropyl)-3,4-dimethoxy-N-methylphenethylamine there was obtained rac-N-(3,4-dimethoxyphenethyl)$\beta$,N-dimethyl-2-(4-tolyl)-m-dithiane-2-propanamine as a viscous oil.

$C_{26}H_{37}NO_2S_2$: Calc.: C 67.93, H 8.11, N 3.05%. Found: C 68.06, H 8.23, N 3.01%.

EXAMPLE 14

In an analogous manner to that described in Example 9, paragraph (B), from 2-(2-naphthyl)-m-dithiane and rac-N-(3-chloro-2-methylpropyl)-3,4-dimethoxy-N-methylphenethylamine there was obtained a colourless oil which was converted with excess hydrogen chloride in abs. ethyl acetate into rac-N-(3,4-dimethoxyphenethyl)-$\beta$,N-dimethyl-2-(2-naphthyl)-m-dithiane-2-propanamine hydrochloride which separated as a white foam.

$C_{29}H_{37}NO_2S_2$ (free base): Calc.: C 70.26, H 7.52, N 2.83%. Found: C 70.63, H 7.74, N 2.64%.

EXAMPLE 15

(A) A solution of 10.93 g (0.056 mol) of N-methylhomoveratrylamine in 50 ml of abs. dimethylformamide was treated at 5° with 15.7 g of potassium carbonate and 13.6 g (0.056 mol) of (R)-(−)-3-benzyloxy-2-methylpropyl bromide [Helv. Chim. Acta 60, 940, (1977)]. The mixture was stirred at room temperature for 18 hours and then evaporated under reduced pressure. The residue was taken up in a mixture of water and ethyl acetate. The organic extracts were dried over magnesium sulphate and evaporated under reduced pressure. The residue was distilled at 218°/260 Pa. The N-[(S)-3-(benzyloxy)-2-methylpropyl]-3,4-dimethoxy-N-methylphenethylamine, which was obtained as a colourless oil, was used directly in the next step. $[\alpha]_D^{20} = +7.3°$ (c=1, ethanol).

(B) A solution of 12.8 g (0.0358 mol) of N-[(S)-3-(benzyloxy)-2-methylpropyl]-3,4-dimethoxy-N-methylphenethylamine in 50 ml of abs. methanol and 35.8 ml of 2N hydrochloric acid was treated with 1.28 g of 5% palladium/charcoal and hydrogenated at room temperature under atmospheric pressure. The filtered-off solution was evaporated under reduced pressure. The residue was taken up in ethyl acetate and washed with a 5% sodium carbonate solution. After drying and evaporating the organic solvent the oily residue was distilled at 155°/130 Pa. There was obtained (S)-3-[(3,4-dimethoxyphenethyl)methylamino]-2-methyl-1-propanol as a colourless oil, $[\alpha]_D^{20} = +12.6°$ (c=1, ethanol).

$C_{15}H_{25}NO_3$: Calc.: C 67.38, H 9.43, N 5.24%. Found: C 66.92, H 9.52, N 5.33%.

(C) A solution of 5.83 g (0.0218 mol) of (S)-3-[(3,4-dimethoxyphenethyl)methylamino]-2-methyl-1-propanol in 50 ml of methylene chloride was treated with 2.4 ml of thionyl chloride at room temperature, left to stand overnight and then evaporated under reduced pressure. The residue was partitioned between ether and a sodium bicarbonate solution (5%). The organic extracts were dried over magnesium sulphate and evaporated under reduced pressure. From the N-[(S)-3-chloro-2-methylpropyl]-3,4-dimethoxy-N-methylphenethylamine, which separated as an oil, there was obtained by means of hydrogen chloride in ethyl acetate N-[(S)-3-chloro-2-methylpropyl]-3,4-dimethoxy-N-methylphenethylamine hydrochloride as a solid substance with a melting point of 109°–110°, $[\alpha]_D^{20} = -3.5°$ (c=1, ethanol).

$C_{15}H_{24}ClNO_2 \cdot HCl$: Calc.: C 55.90, H 7.82, N 4.34%. Found: C 55.87, H 7.95, N 4.31%.

(D) In an analogous manner to that described in Example 1, paragraph (D), from 2-(3,4-dimethoxyphenyl)-m-dithiane and N-[(S)-3-chloro-2-methylpropyl]-3,4-dimethoxy-N-methylphenethylamine there was obtained a colourless oil which was converted with excess hydrogen chloride in abs. ethyl acetate into (R)-N-(3,4-dimethoxyphenethyl)-2-(3,4-dimethoxyphenyl)-$\beta$,N-dimethyl-m-dithiane-2-propanamine hydrochloride in the form of a white foam.

$C_{27}H_{39}NO_4S_2 \cdot HCl$: Calc.: C 59.81, H 7.44, N 2.58%. Found: C 59.47, H 7.54, N 2.77%.

The corresponding oxalate (1:1) of melting point 131°–132° was crystallized from acetonitrile, $[\alpha]_D^{25} = -19.6°$ (c=1, ethanol).

$C_{27}H_{39}NO_4S_2 \cdot C_2H_2O_4$: Calc.: C 58.47, H 6.94, N 2.35%. Found: C 58.33, H 6.94, N 2.31%.

The corresponding amidosulphate (1:1) was obtained after the usual lyophilization of an aqueous solution of an equivalent amount of the base and sulphamic acid.

$C_{27}H_{39}NO_4S_2 \cdot H_3NO_3S$: Calc.: C 53.80, H 7.02, N 4.65%. Found: C 53.76, H 7.35, N 4.29%.

A solution of 679 mg of (R)-N-(3,4-dimethoxyphenethyl)-2-(3,4-dimethoxyphenyl)-$\beta$,N-dimethyl-m-dithiane-2-propanamine and 508 mg of ascorbic acid in 5 ml of water was lyophilized in the usual manner. The resulting (1:2)-ascorbate was dried at 50° in a high vaccum for 2 days, m.p. 75°, $[\alpha]_D^{25} = +24.7°$ (c=1, ethanol).

$C_{27}H_{39}NO_4S_2 \cdot 2C_6H_8O_6$: Calc.: C 54.60, H 6.46, N 1.63, S 7.47%. Found: C 54.22, H 6.37, N 1.80, S 7.24%.

EXAMPLE 16

(A) In an analogous manner to that described in Example 15, paragraph (A), from N-methylhomoveratrylamine and (S)-(+)-3-benzyloxy-2-methylpropyl bromide [Helv. Chim. Acta 60, 940, (1977)] there was obtained N-[(R)-3-(benzyloxy)-2-methylpropyl]-3,4-dimethoxy-N-methylphenethylamine as a colourless oil which was used directly in the next step. $[\alpha]_D^{20} = -7.0°$ (c=0.9, ethanol).

(B) In an analogous manner to that described in Example 15, paragraph (B), from N-[(R)-3-(benzyloxy)-2-methylpropyl]-3,4-dimethoxy-N-methylphenethylamine there was obtained (R)-3-[(3,4-dimethoxyphenethyl)methylamino]-2-methyl-1-propanol as a colourless oil, $[\alpha]_D^{20} = -12.2°$ (c=1, ethanol).

$C_{15}H_{25}NO_3$: Calc.: C 67.38, H 9.43, N 5.24%, Found: C 66.98, H 9.63, N 5.38%.

(C) In an analogous manner to that described in Example 15, paragraph (C), from (R)-3-[(3,4-dimethoxyphenethyl)methylamino]-2-methyl-1-propanol there was obtained N-[(R)-3-chloro-2-methylpropyl]-3,4-dimethoxy-N-methylphenethylamine as an oil which was converted into the corresponding hydrochloride, a solid substance of melting point 109°–110° (from ethyl acetate), $[\alpha]_D^{20} = +3.5°$ (c=1, ethanol).

$C_{15}H_{24}ClNO_2 \cdot HCl$: Calc.: C 55.90, H 7.82, N 4.35%, Found: C 55.83, H 7.91, N 4.31%.

(D) In an analogous manner to that described in Example 1, paragraph (D), from 2-(3,4-dimethoxyphenyl)-m-dithiane and N-[(R)-3-chloro-2-methylpropyl]-3,4-dimethoxy-N-methylphenethylamine there was obtained (S)-N-(3,4-dimethoxyphenethyl)-2-(3,4-dimethoxyphenyl)-β,N-dimethyl-m-dithiane-2-propanamine hydrochloride as a white foam.

$C_{27}H_{39}NO_4S_2 \cdot HCl$: Calc.: C 59.81, H 7.44, N 2.58%, Found: C 59.69, H 7.59, N 2.58%.

The corresponding oxalate (1:1) of melting point 131°–132° was crystallized from acetonitrile, $[\alpha]_D^{25} = +18.9°$ (c=1, ethanol).

$C_{27}H_{39}NO_4S_2 \cdot C_2H_2O_4$: Calc.: C 58.47, H 6.94, N 2.35, S 10.76%. Found: C 58.41, H 6.76, N 2.15, S 10.79%.

The corresponding amidosulphate (1:1) was obtained after the usual lyophilization of an aqueous solution of the base and sulphamic acid.

$C_{27}H_{39}NO_4S_2 \cdot H_3NO_3S$: Calc.: C 53.80, H 7.02, N 4.65%. Found: C 53.76, H 7.35, N 4.29%.

A solution of 15.55 g (30.7 mmol) of (S)-N-(3,4-dimethoxyphenethyl)-2-(3,4-dimethoxyphenyl)-β,N-dimethyl-m-dithiane-2-propanamine and 10.83 g (61.5 mmol) of ascorbic acid in 75 ml of water was filtered over Norit and lyophilized in the usual manner. The resulting (1:2)-ascorbate was dried at 50° in a high vacuum for 2 days, m.p. 75°, $[\alpha]_D^{25} = +46.1°$ (c=1, ethanol).

$C_{27}H_{39}NO_4S_2 \cdot 2C_6H_8O_6$: Calc.: C 54.60, H 6.46, N 1.63, S 7.47%. Found: C 54.43, H 6.58, N 1.58, S 7.14%.

EXAMPLE 17

(A) In an analogous manner to that described in Example 15, paragraph (A), from 1-(3,4-dimethoxyphenyl)cyclopentanemethanamine and (S)-(+)-3-benzyloxy-2-methylpropyl bromide there was obtained (R)-(−)-N-(3-benzyloxy-2-methylpropyl)-1-(3,4-dimethoxyphenyl)-N-methylcyclopentanemethanamine as a colourless oil which was used directly in the next step. $[\alpha]_D^{20} = -2.0°$ (c=1, ethanol).

(B) In an analogous manner to that described in Example 15, paragraph (B), from (R)-(−)-N-(3-benzyloxy-2-methylpropyl)-1-(3,4-dimethoxyphenyl)-N-methylcyclopentanemethanamine there was obtained (R)-3-[[[1-(3,4-dimethoxyphenyl)cyclopentyl]methyl]methylamino]-2-methyl-1-propanol as a colourless oil which was used directly in the next step. $[\alpha]_D^{20} = -27.7°$ (c=1, ethanol).

(C) In an analogous manner to that described in Example 15, paragraph (C), from (R)-3-[[[1-(3,4-dimethoxyphenyl)cyclopentyl]methyl]methylamino]-2-methyl-1-propanol there was obtained (R)-(−)-N-(3-chloro-2-methylpropyl)-1-(3,4-dimethoxyphenyl)-N-methylcyclopentanemethanamine as a colourless oil which was used directly in the next step. $[\alpha]_D^{20} = -21.5°$ (c=1, ethanol).

(D) In an analogous manner to that described in Example 1, paragraph (D), from 2-(3,4-dimethoxyphenyl)-m-dithiane and (R)-(−)-N-(3-chloro-2-methylpropyl)-1-(3,4-dimethoxyphenyl)-N-methylcyclopentanemethanamine there was obtained (S)-(+)-2-(3,4-dimethoxyphenyl)-N-[[(1-(3,4-dimethoxyphenyl)cyclopentyl]methyl]β,N-dimethyl-m-dithiane-2-propanamine as a viscous oil.

$C_{31}H_{45}NO_4S_2$: Calc.: C 66.51, H 8.10, N 2.50%. Found: C 66.91, H 8.30, N 2.36%.

EXAMPLE 18

(A) 25.7 g (1.1 mol eq.) of sodium in small pieces were added gradually to a solution of 198 g (1.1 mol) of homoveratronitrile in 500 ml of diethyl carbonate in such a manner that the temperature remained at approximately 100°. Thereafter, the reaction mixture was heated to reflux for 1 hour, evaporated under reduced pressure, treated with cooled water, acidified with 70 ml of glacial acetic acid and extracted with ether. The combined organic extracts were dried and evaporated. The residual oil was distilled in a high vacuum, whereby ethyl 3,4-dimethoxyphenylcyanoacetate was obtained, b.p. 170°–172°/70 Pa. HPLC purity >99%.

(B) 124.5 g (0.5 mol) of ethyl 3,4-dimethoxyphenylcyanoacetate in 160 ml of abs. dimethylformamide were added at 15°–20° while stirring to a suspension of 84.5 g (0.753 mol) of potassium tert-butylate in 300 ml of abs. dimethylformamide. After one hour 83.5 ml of 1-bromo-3-chloropropane were slowly added dropwise, whereby the temperature amounted to 15°–20°. After 16 hours the reaction mixture was evaporated in a high vacuum. The residue was partitioned between ether and an aqueous saturated ammonium chloride solution. The combined organic extracts were dried and evaporated under reduced pressure. The oily residue was distilled in a high vacuum, whereby 145.7 g of ethyl [γ-chloropropyl-3,4-dimethoxyphenyl]cyanoacetate were obtained, b.p. 195°–201°/80 Pa.

(C) A solution of 145.7 g (0.44 mol) of ethyl [γ-chloropropyl-3,4-dimethoxyphenyl[cyanoacetate in 100 ml of abs. tetrahydrofuran was added within 30 minutes while cooling slightly and stirring vigorously to a suspension of 50.2 g (0.45 mol) of potassium tertbutylate in 150 ml of abs. tetrahydrofuran, whereby the reaction solution became violet in colour. After one hour the solution was evaporated under reduced pressure and the residue was partitioned between ether and a saturated ammonium chloride solution. The organic extracts were dried and evaporated under reduced pressure. The oily residue was distilled in a high vacuum, whereby 1-(3,4-dimethoxyphenyl)cyclobutanecarbonitrile was obtained, b.p. 162°–165°/80 Pa.

(D) 21.7 g (0.387 mol) of potassium hydroxide were added to a solution of 84.0 g (0.387 mol) of 1-(3,4-dimethoxyphenyl)cyclobutanecarbonitrile in 100 ml of ethylene glycol and the mixture was heated to 150° for 18 hours. The reaction solution was then concentrated to 40 ml under a high vacuum, diluted with cold water and extracted with ether. The aqueous solutions were combined, acidified with 3N hydrochloric acid and extracted four times with ether. The ether extracts were dried and evaporated under reduced pressure. There was thus obtained 1-(3,4-dimethoxyphenyl)cyclobutanecarboxylic acid as a colourless oil with a purity of 95.5% determined by HPLC.

The corresponding dicyclohexylamine salt (1:1) could be obtained as a white solid of melting point 119°–120° from ether.

$C_{25}H_{39}NO_4$: Calc.: C 71.91, H 9.41, N 3.35%, Found: C 71.70, H 9.55, N 3.32%.

(E) A solution of the above acid (66.1 g, 0.28 mol) in 50 ml of toluene was treated with 41 ml of thionyl chloride and the mixture was heated to reflux for 2 hours and thereafter evaporated under reduced pressure. The residue was diluted with 50 ml of toluene and the solution was again evaporated under reduced pressure. The residual oil was dissolved in 200 ml of abs. ether and treated slowly while cooling at approximately 5° with 31 ml of methylamine condensed at −20°. The mixture was stirred at room temperature overnight and then partitioned between ether and 1N sodium hydroxide solution. The combined organic extracts were dried and evaporated under reduced pressure. There was thus obtained 1-(3,4-dimethoxyphenyl)-N-methylcyclobutanecarboxamide which had a purity of 91.6% determined by HPCL and which was used directly in the next step without further purification.

(F) A solution of 64.4 g (0.26 mol) of the above N-methylamide in 200 ml of abs. tetrahydrofuran was added dropwise while stirring to a suspension of 15.5 g of lithium aluminium hydride in 400 ml of abs. tetrahydrofuran. After heating to reflux for 24 hours a further 10.0 g of lithium aluminium hydride were added and the suspension was heated to reflux for a further 2.5 hours. After cooling to 5° the suspension was treated cautiously with a saturated aqueous sodium sulphate solution. The precipitate which thereby resulted was filtered off and washed several times with tetrahydrofuran. The organic solutions were evaporated and the oily residue was distilled in a high vacuum. There was thus obtained 1-(3,4-dimethoxyphenyl)-N-methylcyclobutanemethanamine as a colourless oil, b.p. 123°–124°/8 Pa.

The corresponding hydrochloride with a melting point of 233°–234° was obtained using hydrogen chloride/dioxan.

(G) In an analogous manner to that described in Example 1, paragraph (C), from 1-(3,4-dimethoxyphenyl)-N-methylcyclobutanemethanamine and 1-bromo-3-chloropropane there was obtained N-(3-chloropropyl)-1-(3,4-dimethoxyphenyl)cyclobutanemethanamine as a viscous oil (b.p. 170°/260 Pa) which was used directly in the next step.

(H) In an analogous manner to that described in Example 1, paragraph (D), from 2-(3,4-dimethoxyphenyl)-m-dithiane and N-(3-chloropropyl)-1-(3,4-dimethoxyphenyl)cyclobutanemethanamine there was obtained 2-(3,4-dimethoxyphenyl)-N-[[1-(3,4-dimethoxyphenyl)cyclobutyl]methyl]-N-methyl-m-dithiane-2-propanamine as a viscous oil.

$C_{29}H_{41}NO_4S_2$: Calc.: C 65.50, H 7.77, N 2.63%, Found: C 65.28, H 7.90, N 2.53%.

EXAMPLE 19

In an analogous manner to that described in Example 1, paragraph (D), from 2-(3,4,5-trimethoxyphenyl)-m-dithiane and N-(3-chloropropyl)-1-(3,4-dimethoxyphenyl)cyclobutanemethanamine there was obtained N-[[1-(3,4-dimethoxyphenyl)cyclobutyl]methyl]-N-methyl-2-(3,4,5-trimethoxyphenyl)-m-dithiane-2-propanamine hydrochloride as a solid.

$C_{30}H_{43}NO_5S_2 \cdot HCl$: Calc.: C 60.23, H 7.41, N 2.34%. Found: C 60.19, H 7.44, N 2.35%.

EXAMPLE 20

In an analogous manner to that described in Example 1, paragraph (D), from 2-(3,4-ethylenedioxyphenyl)-m-dithiane and N-(3-chloropropyl)-1-(3,4-dimethoxyphenyl)cyclobutanemethanamine there was obtained 2-(1,4-benzodioxan-6-yl)-N-[[1-(3,4-dimethoxyphenyl)cyclobutyl]methyl]-N-methyl-m-dithiane-2-propanamine hydrochloride as a solid.

$C_{29}H_{39}NO_4S_2 \cdot HCl$: Calc.: C 61.52, H 7.12, N 2.47% Found: C 60.95, H 7.60, N 2.41%.

EXAMPLE 21

In an analogous manner to that described in Example 1, paragraph (D), from 2-(3,4-dimethylphenyl)-m-dithiane and N-(3-chloropropyl)-1-(3,4-dimethoxyphenyl)cyclobutanemethanamine there was obtained N-[[1-(3,4-dimethoxyphenyl)cyclobutyl]methyl]-2-(3,4-dimethylphenyl)-N-methyl-m-dithiane-2-propanamine hydrochloride as a solid.

$C_{29}H_{41}NO_2S_2 \cdot HCl$: Calc.: C 64.96, H 7.90, N 2.61% Found: C 64.31, H 7.97, N 2.45%.

EXAMPLE 22

In an analogous manner to that described in Example 1, paragraph (D), from 2-(3,5-dimethoxyphenyl)-m-dithiane and N-(3-chloropropyl)-1-(3,4-dimethoxyphenyl)cyclobutanemethanamine there was obtained N-[[1-(3,4-dimethoxyphenyl)cyclobutyl]methyl]-2-(3,5-dimethoxyphenyl)-N-methyl-m-dithiane-2-propanamine as a viscous oil.

$C_{29}H_{41}NO_4S_2$: Calc.: C 65.50, H 7.77, N 2.63%, Found: C 64.98, H 7.82, N 2.56%.

EXAMPLE 23

In an analogous manner to that described in Example 1, paragraph (D), from 2-(4-chlorophenyl)-m-dithiane and N-(3-chloropropyl)-1-(3,4-dimethoxyphenyl)cyclobutanemethanamine there was obtained 2-(4-chlorophenyl)-N-[[1-(3,4-dimethoxyphenyl)cyclobutyl]methyl]-N-methyl-m-dithiane-2-propanamine hydrochloride as a solid.

$C_{27}H_{36}ClNO_2S_2 \cdot HCl$: Calc.: C 59.76, H 6.87, N 2.58%, Found: C 59.75, H 7.05, N 2.55%.

EXAMPLE 24

(A) A mixture of 40.6 g (0.173 mol) of 1-(3,4-dimethoxyphenyl)-N-methylcyclobutanemethanamine and 29.8 g (0.123 mol) of (S)-(+)-3-benzyloxy-2-methylpropyl bromide [Helv. Chim. Acta 60, 940 (1977)] was heated to 120° for 2.5 hours while stirring well. After cooling the mixture to room temperature 200 ml of ether were added. The precipitate which thereby formed was filtered off under suction and washed with ether. The ethereal solution was extracted three times with 1N hydrochloric acid, the acidic extracts were made basic with 1N sodium hydroxide solution and extracted three times with ether. The ether extracts were dried, evaporated and chromatographed on silica gel with n-hexane/ether (1:1) as the eluting agent. There was thus obtained N-[(R)-3-(benzyloxy)-2-methylpropyl]-3,4-dimethoxyphenyl-N-methylcyclobutanemethanamine as a colourless oil, $[\alpha]_D^{25} = -9.2°$ (c=0.6, ethanol).

$C_{25}H_{35}NO_3$: Calc.: C 75.53, H 8.87, N 3.52%. Found: C 75.26, H 8.96, N 3.49%.

(B) A solution of 35.7 g (0.09 mol) of N-[(R)-3-(benzyloxy)-2-methylpropyl]-3,4-dimethoxyphenyl-N-methylcyclobutanemethanamine and 10.4 ml of benzyl chloride in 300 ml of abs. ethanol was treated under argon with 3.6 g of 10% palladium/charcoal and hydrogenated at room temperature and under atmospheric pressure until the hydrogen uptake was complete. After removing the catalyst by suction filtration the colourless solution was evaporated under reduced pressure. The oily residue was freed from organic solvents in a high vacuum for 24 hours. There was thus obtained (R)-3-[[[1-(3,4-dimethoxyphenyl)cyclobutyl]methyl]-methylamino]-2-methyl-1-propanol as a colourless oil, $[\alpha]_D^{25} = -32.2°$ (c=1, ethanol).

$C_{18}H_{29}NO_3$: Calc.: C 70.32, H 9.51, N 4.56% Found: C 69.91, H 9.54, N 4.55%.

(C) A solution of 26.7 g (0.087 mol) of (R)-3-[[[-(3,4-dimethoxyphenyl)cyclobutyl]methyl]methylamino]-2-methyl-1-propanol in 160 ml of abs. methylene chloride was treated firstly with 87 ml of 1N hydrochloric acid in abs. methylene chloride and then with 12.6 ml of thionyl chloride. This solution was stirred at room temperature overnight and thereafter concentrated under reduced pressure. The residue was partitioned between ether and a 5% sodium carbonate solution and the organic extracts were dried and evaporated under reduced pressure. The oily residue was freed from organic solvents in a high vacuum at room temperature. There was thus obtained N-[(R)-3-chloro-2-methylpropyl]-1-(3,4-dimethoxyphenyl)-N-methylcyclobutanemethanamine as a colourless oil with a purity of 98.8% determined by HPLC, $[\alpha]_D^{25} = -23.2°$ (c=1, ethanol).

$C_{18}H_{28}ClNO_2$: Calc.: C 66.34, H 8.66, N 4.30, Cl 10.88%. Found: C 66.44, H 8.90, N 4.30, Cl 10.56%.

(D) A solution of 34.6 g (0.135 mol) of 2-(3,4-dimethoxyphenyl)-m-dithiane in 200 ml of abs. tetrahydrofuran was cooled to −78° in a sulphonation flask while gassing with dry argon and treated dropwise within 15 minutes with 84 ml (0.135 mol) of a solution of butyllithium in hexane, whereby the temperature was held at −78°. Thereafter, the solution was stirred at −20° for 1 hour and then again cooled to −78° and treated dropwise with a solution of 29.32 g (0.09 mol) of N-[(R)-3-chloro-2-methylpropyl]-1-(3,4-dimethoxyphenyl)-N-methylcyclobutanemethanamine in 75 ml of abs. tetrahydrofuran. After 16 hours at −20° and 2 hours at room temperature the solution was cooled to −10° and treated with 100 ml of a saturated ammonium chloride solution. The mixture was concentrated to a volume of 120 ml under reduced pressure and thereafter extracted with ether. The ethereal extracts were extracted four times with 3N hydrochloric acid and twice with water. The aqueous extracts were treated firstly with ice and then with 6N sodium hydroxide solution to pH 13 and extracted four times with ether. The ethereal extracts were dried over magnesium sulphate, filtered and evaporated under reduced pressure. The residual oil was chromatographed on silica gel 60 with chloroform/ethanol/acetic acid (190:10:5) as the eluting agent. After evaporation of the solvent mixture there was obtained a colourless oil which was freed from organic solvents in a high vacuum at room temperature for 24 hours. The thus-obtained (S)-(+)-2-(3,4-dimethoxyphenyl)-N-[[1-(3,4-dimethoxyphenyl)cyclobutyl]methyl]-β,N-dimethyl-m-dithiane-2-propanamine has a $[\alpha]_D^{25}$ value of +3.75° (c=0.4, ethanol).

$C_{30}H_{43}NO_4S_2$: Calc.: C 66.02, H 7.94, N 2.57%. Found: C 66.00, H 7.95, N 2.47%.

The base was converted into the corresponding hydrochloride, a colourless foam, $[\alpha]_D^{25} = +4.4°$ (c=1, ethanol).

$C_{30}H_{43}NO_4S_2\cdot HCl$: Calc.: C 61.88, H 7.62, N 2.41, S 11.01%, Found: C 61.31, H 7.57, N 2.38, S 10.91%.

546 mg (1 mmol) of the above-named base and 98 mg (1 mmol) of sulphamic acid were stirred in 10 ml of water at room temperature until a clear solution was obtained. This solution was frozen at −20° and lyophilized in a high vacuum. The solid residue was dried in a high vacuum for 24 hours, whereby (S)-2-(3,4-dimethoxyphenyl)-N-[[1-(3,4-dimethoxyphenyl)cyclobutyl]methyl]-β,N-dimethyl-m-dithiane-2-propanamide amidosulphate (1:1) was obtained, $[\alpha]_D^{25} = +2.2°$ (c=1, ethanol).

$C_{30}H_{43}NO_4S_2\cdot H_3NO_3S$: Calc.: C 56.05, H 7.21, N 4.36, S 14.96%, Found: C 55.35, H 7.32, N 4.64, S 15.14%.

EXAMPLE 25

(A) in an analogous manner to that described in Example 24, paragraph (A), from 1-(3,4-dimethoxyphenyl)-N-methylcyclobutanemethanamine and (R)-(−)-3-benzyloxy-2-methylpropyl bromide [Helv. Chim. Acta 60, 940 (1977)] there was obtained N-[(S)-3-(benzyloxy)-2-methylpropyl]-3,4-dimethoxyphenyl-N-methylcyclobutanemethanamine as a colourless oil with a purity of 97.5% determined by HPLC, $[\alpha]_D^{25} = +9.4°$ (c=0.6, ethanol).

(B) In an analogous manner to that described in Example 24, paragraph (B), from N-[(S)-3-(benzyloxy)-2-methylpropyl]-3,4-dimethoxyphenyl-N-methylcyclobutanemethanamine, hydrogen and palladium-on-charcoal there was obtained (S)-3-[[[1-(3,4-dimethoxyphenyl)cyclobutyl]methyl]methylamino]-2-methyl-1-propanol as a colourless oil, $[\alpha]_D^{25} = +29.9°$ (c=0.7, ethanol).

(C) In an analogous manner to that described in Example 24, paragraph (C), from (S)-3-[[[1-(3,4-dimethoxyphenyl)cyclobutyl]methyl]methylamino]-2-methyl-1-propanol and thionyl chloride there was obtained N-[(S)-3-chloro-2-methylpropyl]-1-(3,4-dimethoxyphenyl)-N-methylcyclobutanemethanamine as a colourless oil with a purity of approximately 100% determined by HPLC, $[\alpha]_D^{25} = +21.9°$ (c=0.9, ethanol), which was used directly in the next step.

(D) In an analogous manner to that described in Example 24, paragraph (D), from 2-(3,4-dimethoxyphenyl)-m-dithiane, butyllithium and N-[(S)-3-chloro-2-methylpropyl]-1-(3,4-dimethoxyphenyl)-N-methylcyclobutanemethanamine there was obtained (R)-(−)-2-(3,4-dimethoxyphenyl)-N-[[1-(3,4-dimethoxyphenyl)cyclobutyl]methyl]-β,N-dimethyl-m-dithiane-2-propanamide, $[\alpha]_D^{25} = -3.3°$ (c=3, ethanol).

$C_{30}H_{43}NO_4S_2$: Calc.: C 66.02, H 7.94, N 2.57, S 11.75%. Found: C 66.17, H 8.05, N 2.48, S 11.68%.

The base was converted into the corresponding hydrochloride, a colourless foam.

$C_{30}H_{43}NO_4S_2 \cdot HCl$: Calc.: C 61.88, H 7.62, N 2.41, S 11.01, Cl 6.09%. Found: C 61.40, H 7.94, N 2.32, S 10.73, Cl 6.66%.

In an analogous manner to that described in Example 24, paragraph (D), last section, from the base described above and sulphamic acid there was obtained (R)-2-(3,4-dimethoxyphenyl)-N-[[1-(3,4-dimethoxyphenyl)cyclobutyl]methyl]-β,N-dimethyl-m-dithiane-2-propanamine amidosulphate (1:1).

EXAMPLE 26

(A) In an analogous manner to that described in Example 1, paragraph (C), from 1-(3,4-dimethoxyphenyl)-N-methylcyclobutanemethylamine and 1-bromo-2-methyl-3-chloropropane there was obtained rac-N-(3-chloro-2-methylpropyl)-1-(3,4-dimethoxyphenyl)-N-methylcyclobutanemethanamine as a viscous oil (b.p. 150°/260 Pa) which was used directly in the next step.

(B) In an analogous manner to that described in Example 1, paragraph (D), from 2-(3,4,5-trimethoxyphenyl)-m-dithiane and rac-N-(3-chloro-2-methylpropyl)-1-(3,4-dimethoxyphenyl)-N-methylcyclobutanemethanamine there was obtained rac-N-[[1-(3,4-dimethoxyphenyl)cyclobutyl]methyl]-β,N-dimethyl-2-(3,4,5-trimethoxyphenyl)-m-dithiane-2-propanamine as a viscous oil.

$C_{31}H_{45}NO_5S_2$: Calc.: C 64.67, H 7.88, N 2.43%. Found: C 64.65, H 8.19, N 2.35%.

EXAMPLE 27

In an analogous manner to that described in Example 1, paragraph (D), from 2-(4-chlorophenyl)-m-dithiane and rac-N-(3-chloro-2-methylpropyl)-1-(3,4-dimethoxyphenyl)-N-methylcyclobutanemethanamine there was obtained rac-2-(4-chlorophenyl)-N-[[1-(3,4-dimethoxyphenyl)cyclobutyl]methyl]-β,N-dimethyl-m-dithiane-2-propanamine as a viscous oil.

$C_{28}H_{38}ClNO_2S_2$: Calc.: C 64.65, H 7.36, N 2.69%. Found: C 65.22, H 7.54, N 2.74%.

EXAMPLE 28

In an analogous manner to that described in Example 1, paragraph (D), from 2-(3,4-dimethoxyphenyl)-m-dithiane and rac-N-(3-chloro-2-methylpropyl)-1-(3,4-dimethoxyphenyl)-N-methylcyclobutanemethanamine there was obtained rac-2-(3,4-dimethoxyphenyl)-N-[[1-(3,4-dimethoxyphenyl)cyclobutyl]methyl]-β,N-dimethyl-m-dithiane-2-propanamine as a viscous oil.

$C_{30}H_{43}NO_4S_2$: Calc.: C 66.02, H 7.94, N 2.57% Found: C 65.99, H 8.03, N 2.43%.

EXAMPLE 29

(A) In an analogous manner to that described in Example 1, paragraph (A), from 1-(4-chlorophenyl)cyclobutanecarbonitrile (prepared from 4-chlorophenylacetonitrile according to J. Org. Chem. 36, 1308 (1971)) there was obtained 1-(4-chlorophenyl)cyclobutanemethanamine as a colourless oil (b.p. 125°/650 Pa) which was used directly in the next step.

(B) In an analogous manner to that described in Example 1, paragraph (B), from 1-(4-chlorophenyl)cyclobutanemethanamine there was obtained 1-(4-chlorophenyl)-N-methylcyclobutanemethanamine as a colourless oil (b.p. 108°/260 Pa) which was used directly in the next step.

(C) In an analogous manner to that described in Example 1, paragraph (C), from 1-(4-chlorophenyl)-N-methylcyclobutanemethanamine and 1-bromo-3-chloropropane there was obtained N-(3-chloropropyl)-1-(4-chlorophenyl)cyclobutanemethanamine as a viscous oil which was used directly in the next step.

(D) In an analogous manner to that described in Example 1, paragraph (D), from 2-(3,4,5-trimethoxyphenyl)-m-dithiane and N-(3-chloropropyl)-1-(4-chlorophenyl)cyclobutanemethanamine there was obtained N-[[1-(4-chlorophenyl)cyclobutyl]methyl]-N-methyl-2-(3,4,5-trimethoxyphenyl)-m-dithiane-2-propanamine hydrochloride as a solid.

$C_{28}H_{38}ClNO_3S_2 \cdot HCl$: Calc.: C 58.73, H 6.86, N 2.45%. Found: C 58.02, H 7.29, N 2.27%.

EXAMPLE 30

In an analogous manner to that described in Example 1, paragraph (D), from 2-(4-chlorophenyl)-m-dithiane and N-(3-chloropropyl)-1-(4-chlorophenyl)cyclobutanemethanamine there was obtained 2-(4-chlorophenyl)-N-[[1-(4-chlorophenyl)cyclobutyl)methyl]-N-methyl-m-dithiane-2-propanamine as a viscous oil.

$C_{25}H_{31}Cl_2NS_2$: Calc.: C 62.48, H 6.50, N 2.91%. Found: C 62.69, H 6.63, N 2.82%.

EXAMPLE 31

In an analogous manner to that described in Example 1, paragraph (D), from 2-(3,4-dimethoxyphenyl)-m-dithiane and N-(3-chloropropyl-1-(4-chlorophenyl)cyclobutanemethanamine there was obtained N-[(1-(4-chlorophenyl)cyclobutyl]methyl]-2-(3,4-dimethoxyphenyl)-N-methyl-m-dithiane-2-propanamine as a viscous oil.

$C_{27}H_{36}ClNO_2S_2$: Calc.: C 64.07, H 7.17, N 2.77%. Found: C 63.97, H 7.37, N 2.64%.

EXAMPLE 32

(A) In an analogous manner to that described in Example 1, paragraph (C), from 1-(4-chlorophenyl)-N-methylcyclobutanemethanamine and 1-bromo-2-methyl-3-chloropropane there was obtained rac-N-(3-chloro-2-methylpropyl)-1-(4-chlorophenyl)-N-methylcyclobutanemethanamine as a viscous oil which was used directly in the next step.

(B) In an analogous manner to that described in Example 1, paragraph (D), from 2-(3,4-dimethoxyphenyl)-m-dithiane and rac-N-(3-chloro-2-methylpropyl)-1-(4-chlorophenyl)-N-methylcyclobutanemethanamine there was obtained rac-N-[[1-(4-chlorophenyl)cyclobutyl]methyl]-2-(3,4-dimethoxyphenyl)-β,N-dimethyl-m-dithiane-2-propanamine hydrochloride as a solid.

$C_{28}H_{38}ClNO_2S_2 \cdot HCl$: Calc.: C 60.42, H 706, N 2.52%. Found: C 60.64, H 7.39, N 2.42%.

EXAMPLE 33

In an analogous manner to that described in Example 1, paragraph (D), from 2-(3,4-ethylenedioxyphenyl)-m-dithiane and rac-N-(3-chloro-2-methylpropyl)-1-(4-chlorophenyl)-N-methylcyclobutanemethanamine there was obtained rac-2-(1,4-benzodioxan-6-yl)-N-[[1-(4-chlorophenyl)cyclobutyl]methyl]-β,N-dimethyl-m-dithiane-2-propanamine as a viscous oil.

$C_{28}H_{36}ClNO_2S_2$: Calc.: C 64.90, H 7.00, N 2.70%. Found: C 65.12, H 7.17, N 2.80%.

EXAMPLE 34

In an analogous manner to that described in Example 1, paragraph (D), from 2-(4-chlorophenyl)-m-dithiane and rac-N-(3-chloro-2-methylpropyl)-1-(4-chlorophenyl)-N-methylcyclobutanemethanamine there was obtained rac-2-(4-chlorophenyl)-N-[[1-(4-chlorophenyl)cyclobutyl]methyl]-β,N-dimethyl-m-dithiane-2-propanamine hydrochloride as a crystalline solid, m.p. 135°-136° (from ethyl acetate).

$C_{26}H_{33}Cl_2NS_2$: Calc.: C 58.81, H 6.45, N 2.64%. Found: C 58.49, H 6.61, N 2.56%.

EXAMPLE A

Tablets

Composition:

| | |
|---|---|
| 1) rac-2-(4-Chlorophenyl)-N-[[1-(4-chlorophenyl)-cyclobutyl]methyl]-β,N-dimethyl-m-dithiane-2-propanamine hydrochloride | 275 mg |
| 2) Powd. lactose | 135 mg |
| 3) White corn starch | 55 mg |
| 4) Povidone K | 15 mg |
| 5) White corn starch | 15 mg |
| 6) Talc | 3 mg |
| 7) Magnesium stearate | 2 mg |
| Tablet weight | 500 mg |

Manufacturing procedure:

1-3 are mixed intensively. The mixture is thereafter moistened with an aqueous solution of 4 and kneaded, and the resulting mass is granulated, dried and sieved. The granulate is mixed with 5-7 and pressed to tablets of suitable size.

EXAMPLE B

Capsules

Composition:

| | |
|---|---|
| 1) rac-2-(4-Chlorophenyl)-N-[[1-(4-chlorophenyl)-cyclobutyl]methyl]-β,N-dimethyl-m-dithiane-2-propanamine hydrochloride | 370 mg |
| 2) Cryst. lactose | 100 mg |
| 3) White corn starch | 20 mg |
| 4) Talc | 9 mg |
| 5) Magnesium stearate | 1 mg |
| Capsule fill weight | 500 mg |

The active ingredient is mixed intensively with the lactose. This mixture is thereafter admixed with the corn starch, the talc and the magnesium stearate and the mixture is filled into capsules of suitable size.

EXAMPLE C

Injection solution

| | |
|---|---|
| 1) N-[[1-(3,4-Dimethoxyphenyl)cyclohexyl]-methyl]-2-(3,4-dimethoxyphenyl)-N-methyl-m-dithiane-2-propanamine hydrochloride | 40 mg |
| 2) Purest cryst. sodium chloride | 42,5 mg |
| 3) Water for injection | ad 5 ml |

EXAMPLE D

Infusion bottle 3 mg of vincristine sulphate and 300 mg of N-[[1-(3,4-dimethoxyphenyl)cyclohexyl]methyl]-2-(3,4-dimethoxyphenyl)-N-methyl-m-dithiane-2-propanamine hydrochloride are dissolved in 250 ml of physiological saline, sterilized and filled into an infusion bottle under sterile conditions.

EXAMPLE E

Tablets

Composition:

| | |
|---|---|
| 1) (R)-(−)-N-(3,4-Dimethoxyphenethyl)-2-(3,4-dimethoxyphenyl)-β,N-dimethyl-m-dithiane-2-propanamine amidosulphate | 200 mg |
| 2) Powd. lactose | 110 mg |
| 3) White corn starch | 55 mg |
| 4) Povidone K | 15 mg |
| 5) White corn starch | 15 mg |
| 6) Talc | 3 mg |
| 7) Magnesium stearate | 2 mg |
| Tablet weight | 400 mg |

Manufacturing procedure 1-3 are mixed intensively. The mixture is thereafter moistened with an aqueous solution of 4 and kneaded, and the resulting mass is granulated, dried and sieved. The granulate is mixed with 5-7 and pressed to tablets of suitable size.

EXAMPLE F

Tablets

Composition:

| | |
|---|---|
| 1) (S)-(+)-N-(3,4-Dimethoxyphenethyl)-2-(3,4-dimethoxyphenyl)-β,N-dimethyl-m-dithiane-2-propanamine (1:2)-ascorbate | 200 mg |
| 2) Powd. lactose | 110 mg |
| 3) White corn starch | 55 mg |
| 4) Povidone K | 15 mg |
| 5) White corn starch | 15 mg |
| 6) Talc | 3 mg |
| 7) Magnesium stearate | 2 mg |
| Tablet weight | 400 mg |

Manufacturing procedure 1-3 are mixed intensively. The mixture is thereafter moistened with an aqueous solution of 4 and kneaded, and the resulting mass is granulated, dried and sieved. The granulate is mixed with 5-7 and pressed to tablets of suitable size.

EXAMPLE G

When the procedures described in Examples A-F are followed, tablets, capsules, injection solutions and, respectively, infusion bottles can be manufactured from the following, likewise preferred compounds and their pharmaceutically usable salts:

rac-N-[[1-(3,4-Dimethoxyphenyl)cyclohexyl]methyl]-β,N-dimethyl-2-(3,4,5-trimethoxyphenyl)-m-dithiane-2-propanamine, 2-(3,4-dimethoxyphenyl)-N-[[1-(3,4-dimethoxyphenyl)cyclopentyl]methyl]-N-methyl-m-dithiane-2-propanamine, rac-N-(4-chlorophenethyl)-2-(4-chlorophenyl)-β,N-dimethyl-m-dithiane-2-propanamine, rac-N-(3,4-dimethoxyphenethyl)-β,N-dimethyl-2-(2-naphthyl)-m-dithiane-2-propanamine, (S)-(+)-2-(3,4-dimethoxyphenyl)-N-[[1-(3,4-dimethoxyphenyl)cyclobutyl]methyl]-β,N-dimethyl-m-dithiane-2-propanamine and (R)-(−)-2-(3,4-dimethoxyphenyl)-N-[[1-(3,4-dimethoxyphenyl)cyclobutyl]methyl]-β,N-dimethyl-m-dithiane-2-propanamine.

We claim:

1. A dithiane comprising a compound of the formula

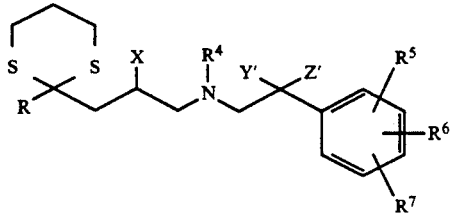

I

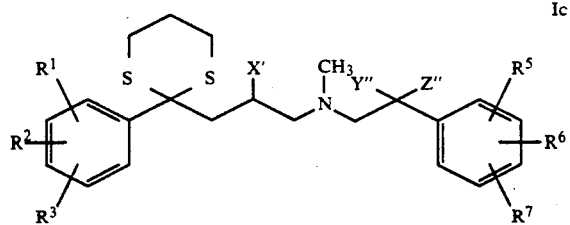

Ic wherein $R^1$, $R^2$, $R^3$, $R^5$, $R^6$ and $R^7$ are as described; X' is hydrogen or methyl and Y'' and Z'' taken together form di-, tri-, tetra-, or pentamethylene, or an acid addition salt thereof.

4. A dithiane comprising a compound of the formula

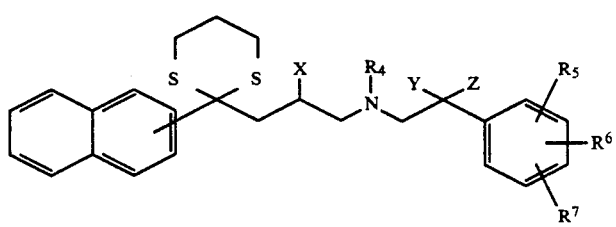

Id wherein $R^4$ is lower alkyl; $R^5$, $R^6$ and $R^7$ are individually hydrogen, halogen, lower alkyl, lower alkoxy or aryl-lower-alkoxy or when two of these residues are adjacent substituents, these substituents can additionally be taken together to form methylenedioxy or ethylenedioxy; X is hydrogen or lower alkyl; and Y and Z when taken together form di-, tri-, tetra-, or pentamethylene; or an acid addition salt thereof.

5. A dithiane of claim 4 wherein X is methyl.

6. A dithiane of claim 3 which has the formula N-[[1-(3,4-Dimethoxyphenyl)cyclohexyl]methyl]-2-(3,4-dimethoxyphenyl)-N-methyl-m-dithiane-2-propanamine.

7. A dithiane of claim 3 which has the formula rac-N-[[1-(3,4-Dimethoxyphenyl)cyclohexyl]methyl]-β,N-dimethyl-2-(3,4,5-trimethoxyphenyl)-m-dithiane-2-propanamine.

8. A dithiane of claim 3 which has the formula 2-(3,4-Dimethoxyphenyl)-N-[[1-(3,4-dimethoxyphenyl)cyclopentyl]methyl]-N-methyl-m-dithiane-2-propanamine.

9. A dithiane of claim 3 which has the formula rac-2-(4-Chlorophenyl)-N-[[1-(4-chlorophenyl)cyclobutyl]methyl]-β,N-dimethyl-m-dithiane-2-propanamine.

10. A dithiane of claim 3 which has the formula (S)-(+)-2-(3,4-Dimethoxyphenyl)-N-[[1-(3,4-dimethoxyphenyl)cyclobutyl]methyl]-β,N-dimethyl-m-dithiane-2-propanamine.

11. A dithiane of claim 3 which has the formula (R)-(−)-2-(3,4-Dimethoxyphenyl)-N-[[1-(3,4-dimethoxyphenyl)cyclobutyl]methyl]-β,N-dimethyl-m-dithiane-2-propanamine.

wherein R is a residue of the formula

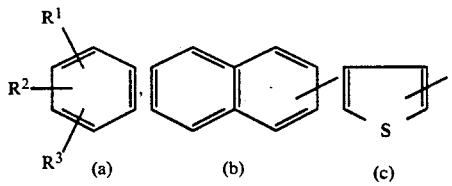

$R^1$, $R^2$, and $R^3$ are individually hydrogen, halogen, lower alkyl, lower alkoxy, aryl-lower-alkoxy, lower alkylthio, trifluoromethyl or di-lower-alkylamino or when two of these residues are adjacent substituents, these substituents can additionally be taken together to form methylenedioxy, ethylenedioxy, trimethylene or tetramethylene; $R^4$ is lower alkyl; $R^5$, $R^6$ and $R^7$ are individually hydrogen, halogen, lower alkyl, lower alkoxy or aryl-lower-alkoxy or when two of these residues are adjacent substituents, these substituents can additionally be taken together to form methylenedioxy or ethylenedioxy; X is hydrogen or lower alkyl; and Y' and Z' taken together form di-, tri-, tetra-, or pentamethylene; or an acid addition salt thereof.

2. A dithiane of claim 1 wherein X is methyl.

3. A dithiane of claim 1 having the formula:

* * * * *